United States Patent [19]
Johnsen et al.

[11] 4,134,403
[45] Jan. 16, 1979

[54] EYE DROP DISPENSER ATTACHABLE POSITIONER

[76] Inventors: Frank R. Johnsen, Box 68, Rte. No. 2, Blair, Nebr. 68008; James R. Barta, 1821 Sherwood Cove, Fremont, Nebr. 68025; Eugene J. Colner, 9006 W. 94th St., Overland Park, Kans. 66212

[21] Appl. No.: 810,633

[22] Filed: Jun. 27, 1977

[51] Int. Cl.$^2$ .............................................. A61M 1/00
[52] U.S. Cl. ................................... 128/233; 222/192; 222/420
[58] Field of Search ................. 128/233, 249; 215/100; 222/192, 420

[56] References Cited
U.S. PATENT DOCUMENTS

| | | | |
|---|---|---|---|
| 1,618,724 | 2/1927 | Pearson | 215/100 R |
| 2,676,592 | 4/1954 | Wood | 128/233 |
| 3,439,674 | 4/1969 | Lelicoff | 128/233 |
| 3,521,636 | 7/1970 | Mahoney et al. | 128/233 |
| 3,934,590 | 1/1976 | Campagna et al. | 128/233 |

Primary Examiner—Dalton L. Truluck
Attorney, Agent, or Firm—Hiram A. Sturges

[57] ABSTRACT

An eye drop dispenser attachable positioner having a forward portion having pressure sensitive adhesive means thereon for attaching the positioner to the side of an eye drop dispenser, the positioner having a rearward terminal end portion adapted to engage the upper portion of a person's nose while the positioner is held for steadying and positioning the dispenser preparatory to squeezing eye fluid therefrom.

3 Claims, 3 Drawing Figures

EYE DROP DISPENSER ATTACHABLE POSITIONER

BACKGROUND OF THE INVENTION

Eye drop medicines are very expensive and there has been great waste of such medicines because persons have aimed them badly whereby they miss the eye.

Unfortunately, many people who require eye drop medicine of the expensive types are themselves elderly persons who can least afford to waste expensive medicine.

Many of the elderly have considerable difficulty in controlling their hands with the steadiness required to aim an eye drop dispenser accurately because of loss of coordination due to old age and also palsey.

There has been placed on the market a protrusion extending from an eye drop dispenser in parallelism with the nozzle thereof, the protrusion having an outer end adapted to rest on the upper portion of the nose and being rigidly fixed to the dispenser, and being formed of thermoplastic material of one piece with the dispenser for guiding the positioning of the nozzle so as to dispense fluid at a position to one side of the nose engaging terminal end of the protrusion which is the proper spacing for causing the nozzle to be aimed at the user's eye.

However, the protrusion mentioned has been serving only a single brand of eye drops to the applicant's knowledge, that brand being one that has a very special dispenser with a fluid holding chamber elongated transversely of the direction of fluid ejection so as to provide a place on the rearward end thereof for supporting the protrusion.

The result has been a very highly specialized product serving only a minute portion of the eye medicine dispensing field. The only portion being served has been that portion which uses one single brand of eye drops contained in one single type of special container, the eye drops being a brand that is dispensed without prescription.

However, the vast majority of eye drop conainers are used without any means for their positioning and resulting in the waste of medicine mentioned. Among this vast majority of eye drop containers are the prescription medicine containers which are usually provided with a forward portion which is substantially cylindrical in the usual and common way which bottles have always been made. For these prescription medicines there has been no way heretofore conceived of facilitating their positioning during dispensing.

Also there has been no way conceived heretofore of positioning dispensers of the many dozens if not hundreds of brands of eye medicines which are sold without perscription, the vast majority of which are likewise sold in containers having substantially cylindrical forward portions sometimes called lower portions.

One of the problems in conceiving of a positioner suitable to be attached by a user to a standard eye drop medicine bottle is the problem of how to attach the positioner to the bottle in some way without interfering with the necessary squeezing of the bottle for dispensing the fluid. That is a problem which does not arise in the case of the one-piece protrusion and dispenser bottle bacause the attachment portions and the squeezable flexible dispenser bottle are one and the same.

I have solved this problem with my concept of using flexible pressure sensitive adhesive for securing the body of the positioner to the medicine bottle, the pressure sensitive adhesive being a tape which is itself flexible and, therefore, does not interfere with the squeezing of the bottle for dispensing.

A problem, however, arises in the weakness of the attachment of such a tape to the body of a positioner and which is solved by my concept of having the positioner have an unusually large area at a portion near the tape, the area not being so large as to interfere with the squeezing of the bottle, however, because of the necessary relative lesser flexibility of the large attachment portion and the tape itself.

Another problem resides in the proper positioning of the positioner on the bottle. This I have solved by designing the positioner to be used with the advice that the positioner nose engaging terminal end is to be rested on a flat surface at a time when the terminal end of the nozzel of the bottle is rested on the same flat surface, whereby the nose engageable portion and the nozzle terminal end will be positioned directly to the side of each other, even though the type of bottle involved might be twice as long as a smaller bottle on which the same positioner of this invention must also be able to function.

Still another problem is bottle shape. Many bottles are not cylindrical and, therefore, present side surfaces which are almost flat and end surfaces that are rounded, but which are so narrow and sharply rounded as to present a much different surface to which to attach than is the case with a cylindrical bottle. It is, therefore, an object of this invention to provide my concept of a positioner having a tape attachment portion which is able to adapt itself to bottles of any shape.

I discovered that tapes available are not strong enough. I have conceived that by placing a flexible plastic layer on the outside of the tape and substantially co-extensive with the tape, with the plastic layer of greater strength than the tape and disposed between the tape and the body of the dispenser, that a construction of sufficient strength is provided.

SUMMARY OF THE INVENTION

This invention provides an eye drop dispenser attachable positioner having a body provided with a rearward terminal end nose-engaging surface having a horizontal width sufficient for spanning horizontally across the upper portion of a human user's nose, said body having a forward portion provided with a side surface defining a bottle-facing side surface which is elongated forwardly and rearwardly and which is offset approximately 1½ inches from the center between the sides of said nose-engaging surface so that when said nose-engaging surface is against the upper portion of the nose of the average adult user and an eye drop medicine dispenser bottle, of approximately ⅜ inch from its center to its closest side adjacent to said bottle-facing surface of said body, then the center of the bottle will be disposed approximately on a horizontal line directly forwardly from the eye of an average adult user, and means for attaching an eye dropper medicine bottle to the said bottle-facing side surface of said body, said attaching means having an adhesive bonding means for facing said bottle.

Another advantage is for the positioner to be removable from said bottle without the destruction of said positioner and with the possibility of the reuse of the attaching means on another bottle.

This invention further provides for said adhesive bonding means to be a tape having pressure sensitive adhesive coating on both sides for economy of construction and for flexibility of fitting to the bottle.

A further objective is to provide the body with a greater thickness, as seen in rear elevation, adjacent said side surface than the general thickness of said body.

Still another objective is to provide the construction of said attaching means in the form of a piece of tape, having pressure sensitive adhesive on that side thereof which faces away from said body for attachment to a bottle, and means attaching the pressure sensitive adhesive to said side of said body.

Yet another object is to provide an attachment means as above described and in which tape is involved, but further in which a strip of plastic of substantially greater strength than said tape is attached to that side of said tape which is closest to said body, said strip of plastic being attached to said body, and being flexible for adapting to engage in abutment across the majority of its surface besides of bottles of various shapes.

Another object is to provide the use of tape, each side of which has on it pressure sensitive adhesive.

A BRIEF DESCRIPTION OF THE DRAWINGS

In FIG. 1, a side plan view of an eye drop dispenser is there shown in horizontal position preparatory to a person's tilting their head back to squeeze the dispenser to administer a drop of medicine, the attachable positioner of this invention being shown attached thereto.

DESCRIPTION OF THE PREFERRED EMBODIMENT

Figure 1:
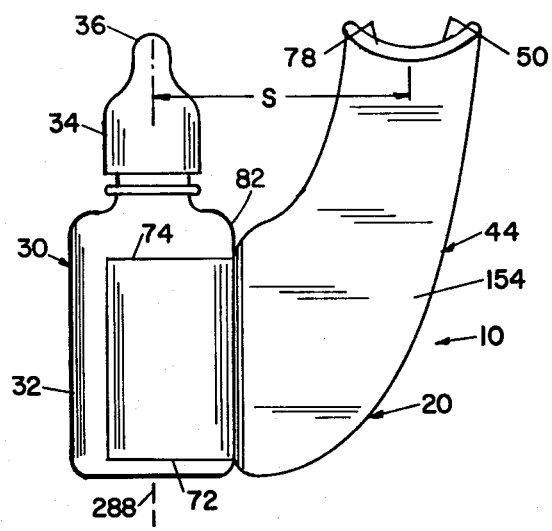

An eye drop dispenser and positioner assembly of this invention is generally indicated at 10 in FIG. 1 and has an eye drop dispenser bottle 30 to which an eye drop dispenser attachable positioner 20 is attached.

Eye drop bottles are, for the most part, provided with a cylindrical lower portion generally indicated at 32 of a diameter of about ¾ of an inch of ⅝ of an inch, or in other words, approximately ¾ of an inch diameter and ⅜ of an inch radius.

The bottles 30 each have a cap 34 having at its forward end an opening 36 through which droplets of eye treatment fluid can exude at times when the bottle is squeezed and for that reason the cylindrical portion 32 is flexible.

The positioner 20 has a body 44 provided with a rearward-terminal-end nose-engaging surface 50 having a horizontal width as seen from left to right in FIG. 1, sufficient for spanning across the upper portion of a human user's nose.

The body 44 has a forward portion 60 provided with a side surface 64, defining a bottle-facing side surface which is elongated forwardly and rearwardly, such as between its forward end 72 and its rearwrd end 74 as seen in FIG. 1.

Figure 2:
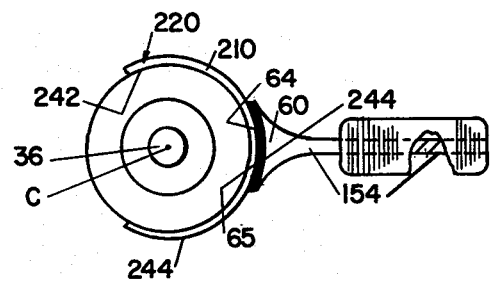
FIG. 2 is a top view of the rearward side of the dispenser and positioner of FIG. 1 as would be seen from the top of the page, a portion of the dispenser being broken away for purposes of illustration.

The side surface 64 has a portion 65 which is closest to the nose-engaging surface 50, offset horizontally from the center 78 of the nose-engaging surface 50, the center 78 being the center between the sides on the right and left of the nose-engaging surface 50, the offset being approximately 1½ inches as measured horizontally along line 5' when looking at the rear of the positioner, so that when the nose-engaging surface 50 is against the upper portion of the nose of the average adult user, then when an eye drop medicine dispenser bottle, such as shown at 30, is disposed with its closest side 82 adjacent to the bottle-facing surface 64 of the positioner 20, then the center of the bottle 30, which latter is shown at C in FIG. 2, will be disposed approximately on a horizontal line directly forwardly from the eye on the average adult user.

In FIG. 2 it can be seen that the nose-engaging surface 50 has a substantial vertical width greater than the central portion 154 of the body 40 to which it is attached for the comfort of the user and for the economy of the body portion 154.

In FIG. 2 it can be seen that the bottle-facing side surface 64 is wider vertically than the central portion 154 of the body 44 so as to provide the surface 64 with a substantial width so that it can be secured to the bottle 30 better.

Figure 3:
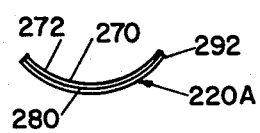
FIG. 3 is a detail showing a part of the positioner shown in the lower left part of FIG. 2, but in sufficient detail to show a laminated structure.

The surface 64 is secured to the bottle 30 either by means of a pressure sensitive adhesive tape 210, defining a flexible securing means 220 or else it is secured by a laminated flexible assembly or a modified flexible securing means 220a shown in FIG. 3.

The tape 210 has pressure sensitive adhesive on its surface 242 which faces the bottle 30 and also has pressure sensitive adhesive 244 on its outer surface and secured to the surface 64. With this construction, the flexibility of the tape 210 permits its removal from one bottle and attachment to another bottle for the repeated use of the positioner 20.

In the laminated modification of FIG. 3, shown at 220a, the flexible attachment 220a has an inner portion 270 which is a tape and which is provided with an adhesive surface 272 on its inner side for engaging the bottle 30 and has on its outer side a very thin flexible, plastic, partially circular member 280 which can be called a mounting member 280. The mounting member 280 is partially circular when seen in the vertical cross-section or when seen from the rearward end of the bottle 32 looking along an axis 288 of the bottle, the extent of the member 280 and of the tape 270, preferably both being sufficient to more than cover half of the outer circumference of the bottle at its cylindrical portion 32, the laminated member 220a being coextensive with the member 220 of FIG. 2 for length so that it can be understood from looking at FIG. 2.

The mounting 280 can be molded separately from and detached to the remainder of the positioner 20 or it can be formed integral and of one piece with the remainder of the positioner 20 but in either case it is attached to the forward portion 60 of the positioner 20 firmly by either one piece attachment or binding means, a numeral 292 in FIG. 3 serving to indicate part of the position of binding means for that purpose.

In operation, the flexibility of the tape 210 or of the laminated structure 220a are either one sufficient to permit the compressing of the flexible bottle portion 32 so that with the postioner in the use position, the operator simply tilts his head back so that the squeezing of the bottle 32 will deposit a drop of fluid directly in his eye.

To do the other eye, the positioner is turned upside down so that its bottle is then on the opposite side from the position shown in FIG. 1.

The stiffer portion of the body in FIG. 2 adjacent to the tape is of a very short width so that the positioner can adapt to square bottles with flat sides. Depending upon the kind of adhesive or bonding means used the portion of the positioner adjacent the tape might be of lesser vertical thickness adjacent to the bottle for adapting it best to fitting against flat sided bottles.

We claim:

1. An eye drop dispenser attachable positioner having a body provided with a rearward-terminal-end nose-engaging surface having a horizontal width sufficient for spanning across the upper portion of a human user's nose, said body having a forward portion provided with a side surface defining a bottle-facing side surface which is elongated forwardly and rearwardly and which is offset from the center between the sides of said nose-engaging surface so that when said nose-engaging surface is against the upper portion of the nose of the average adult user and an eye drop medicine dispenser bottle is disposed with its closest side adjacent to said bottle-facing side surface of said body, then the center of the bottle will be disposed approximately on a horizontal line directly forwardly from the eye of an average adult user, and means for attaching an eye dropper medicine bottle to the said bottle-facing side surface of said body, said attaching means having an adhesive bonding means for facing said bottle and characterized by being removable from said bottle without the destruction of said positioner and with the possibility of the reuse of said attaching means on another bottle.

2. The eye drop dispenser attachable positioner of claim 1 having said attaching means being a tape with pressure sensitive adhesive coating on two sides, one side of said tape being secured to said positioner.

3. The eye drop dispenser attachable positioner of claim 1 in which said body has a thin flexible portion formed in the shape of a part of a cylinder disposed between said bonding means and adjacent portions of said positioner body.

* * * * *